United States Patent [19]

Teunissen et al.

[11] Patent Number: 4,775,755

[45] Date of Patent: * Oct. 4, 1988

[54] PROCESS FOR THE PREPARATION OF PYRIMIDINE AND 2-ALKYLPYRIMIDINE

[75] Inventors: Antonius J. J. M. Teunissen, Geleen; Cornelis G. M. Van De Moesdijk, Spaubeek; Hubertus J. A. V. Delahaye, Voerendaal, all of Netherlands

[73] Assignee: Stamicarbon B. V., Geleen, Netherlands

[*] Notice: The portion of the term of this patent subsequent to May 19, 2004 has been disclaimed.

[21] Appl. No.: 829,491

[22] Filed: Feb. 14, 1986

[30] Foreign Application Priority Data

Feb. 15, 1985 [NL] Netherlands ..................... 8500431
Oct. 12, 1985 [NL] Netherlands ..................... 8502796

[51] Int. Cl.$^4$ .......................................... C07D 239/26
[52] U.S. Cl. ................................................. 544/242
[58] Field of Search ...................... 544/242; 546/252

[56] References Cited

U.S. PATENT DOCUMENTS

| | | | |
|---|---|---|---|
| 3,050,523 | 8/1962 | Erner et al. | 544/242 |
| 4,376,201 | 3/1983 | Pews | 544/242 |
| 4,493,929 | 1/1985 | Pews | 544/242 |
| 4,667,034 | 5/1987 | van de Moesdijk et al. | 544/242 |

FOREIGN PATENT DOCUMENTS 2748976 5/1979 Fed. Rep. of Germany.
930090 7/1963 United Kingdom.

OTHER PUBLICATIONS

Engels, et al., Chemical Abstracts, vol. 81: 82750d (1974).
Okada, et al., Chemical Abstracts, vol. 85:142251m (1976).
Tsuchiya, et al., Chemical Abstracts, vol. 86: 29745h (1977).
Engels, et al., Z. Chem., 1974, 14(5), pp. 202–203 (1974).
Okada, et al., Yakugaku Zasshi, 1976, 96(6), pp. 801–809 (1976).
Tsuchiya, et al., Yakugaku Zasshi, 1976, 96(8), pp. 1005–1012 (1976).

Primary Examiner—Donald G. Daus
Assistant Examiner—Diana G. Rivers
Attorney, Agent, or Firm—Cushman, Darby & Cushman

[57] ABSTRACT

The invention provides a process for the preparation of pyrimidine, 2-methyl- and/or 2-ethylpyrimidine, characterized in that for pyrimidine a nitrogen reactant, chosen from the reaction product of formamide with 1,3-diaminopropane in the liquid phase, 1-amino-3-formamidopropane, 1,4,5,6-tetrahydropyrimidine and/or 1,3-diformamidopropane, that for 2-methylpyrimidine 1-amino-3-acetamidopropane, 2-methyl-1,4,5,6-tetrahydropyrimidine and/or 1,3-diacetamidopropane, and that for 2-ethylpyrimidine 1-amino-3-propionamidopropane, 2-ethyl-1,4,5,6-tetrahydropyrimidine and/or 1,3-dipropionamidopropane is/are contacted with a palladium-containing catalyst, this being effected in the gas phase at a temperature between 200° and 550° C. and in the presence of a carbon monoxide-hydrogen reactant, and that pyrimidine, 2-methyl-and/or 2-ethyl-pyrimidine is recovered from the reaction mixture obtained.

9 Claims, No Drawings

PROCESS FOR THE PREPARATION OF PYRIMIDINE AND 2-ALKYLPYRIMIDINE

The invention relates to a process for the preparation of pyrimidine, 2-methylpyrimidine and/or 2-ethylpyrimidine.

A process as described in the preamble is known from Yakugaku Zasshi 96: 1005–1012 (1976). This article relates mainly to the gas-phase synthesis of 2-alkylpyrimidines from diaminopropane and aldehydes in the presence of four catalysts, viz.: Pd (2%)-$Al_2O_3$, Pt (2%)-$Al_2O_3$ Rh (2%)-$Al_2O_3$ and Pt (1%)-Rh (1%)-$Al_2O_3$. According to said article, in the various ring closure experiments conducted the best results were obtained with the Pt-Rh catalyst and with the Rh catalyst. The Pd catalyst was hardly active. The article incidentally gives a pyrimidine yield from diaminopropane and formaldehyde of 6% (besides 6% 2-methylpyrimidine and 19% 2-ethylpyrimidine). From Table I of the article it can be concluded that the Pt-Rh catalyst was used in this experiment. At the end of their article, the authors explain the low pyrimidine yield by pointing to the instability of the proposed hexahydropyrimidine intermediate as well as to the sensitivity to side-reactions of this intermediate. The authors of the article in general advise against the use of Pd catalysts in ring closure experiments as described by them.

In Yakugaku Zasshi 97: 373–381 (1977) the same research group describes the reaction of diaminopropane with methanol, producing pyrimidine in a 7% yield. Details of this reaction are not given, but the catalyst used probably again was Pt (1%)-$Al_2O_3$. The 2-ethyl- or 2-methylpyrimidine yield is 40–50%.

The invention provides a process for the preparation of pyrimidine, 2-methyl- and/or 2-ethylpyrimidine, characterized in that for pyrimidine a nitrogen reactant, chosen from the reaction product of formamide with 1,3-diaminopropane in the liquid phase, 1-amino-3-formamidopropane, 1,4,5,6-tetrahydropyrimidine and/or 1,3-diformamidopropane, that for 2-methylpyrimidine 1-amino-3-acetamidopropane, 2-methyl-1,4,5,6-tetrahydropyrimidine and/or 1,3-diacetamidopropane, and that for 2-ethylpyrimidine 1-amino-3-propionamidopropane, 2-ethyl-1,4,5,6-tetrahydropyrimidine and/or 1,3-dipropionamidopropane is/are contacted with a palladium-containing catalyst, this being effected in the gas phase at a temperature between 200° and 550° C. and in the presence of a carbon monoxide-hydrogen reactant, and that pyrimidine, 2-methyl- and/or 2-ethyl-pyrimidine is recovered from the reaction mixture obtained.

A carbonmonoxide-hydrogen reactant is understood to be carbon monoxide and hydrogen and/or a compound capable of at least partial decomposition into carbon monoxide and hydrogen under the reaction conditions.

By application of this process, unsubstituted pyrimidine can be prepared in a yield, calculated on the nitrogen reactant, of 40–60%, and 2-methyl- or 2-ethylpyrimidine in a yield of 80–90%.

In the preparation of pyrimidine it is, for that matter, quite possible to recycle unreacted 1,3-diaminopropane or formamide after separation thereof, and to re-use it in the liquid-phase reaction as described above. It is, therefore, particularly the yield that determines the value of the gas-phase conversion as described above.

In itself, the reaction of 1,3-diaminopropane (DAP) with formamide in the liquid phase is known from DE-A No. 2748976. According to said publication, 1-amino-3-formamidopropane, hereinafter referred to as AFP, is formed from the reaction of 1,3-diaminopropane with formamide, whether or not in the presence of an inert solvent, at a temperature between 50° and 200° C. In a second step, AFP can, according to the teaching of DE-A No. 2748976, be converted to 1,4,5,6-tetrahydropyrimidine, hereinafter referred to as THP, by pyrolysis at reduced pressure.

Applicant has, however, found by NMR analysis as well as by analysis by means of mass spectrometry, that the liquid-phase reaction between formamide and a molar excess of 1,3-diaminopropane yields a reaction mixture which (after removal of the excess of 1,3-diaminopropane) contains, besides AFP, also a considerable amount of THP. Experiments have shown that such a mixture may even contain more THP than AFP, calculated on molar basis.

Applicant has further found that the embodiment, in which a twofold molar excess of formamide with 1,3-diaminopropane is used, yields a reaction mixture in which mainly 1,3-diformamidepropane (DFP) is present.

Applicant has subsequently found that both the AFP- and THP-containing mixture and the DFP-containing mixture can be converted in the gas phase to a pyrimidine-containing reaction mixture in a high yield.

The preparation in the liquid phase of acetamidopropanes and/or methyl-1,4,5,6-tetrahydropyrimidines is effected, for instance, by reaction of acetic acid, acetic acid anhydride, acetic acid amide or acetic acid chloride with 1,3-diaminopropane; the propionamidopropanes and/or ethyl-1,4,5,6-tetrahydropyrimidines are prepared in an analogous way from propionic acid derivatives.

Instead of the crude reaction mixture that contains various substances as described above, it is also possible to convert pure (2-alkyl)-1,4,5,6-tetrahydropyrimidines in the gas phase to (2-alkyl)pyrimidine.

Pure THP can be obtained, for instance, by pyrolysis of AFP according to DE-A No. 2748976. The AFP can also be contacted with a known dehydration catalyst, for instance alumina, at elevated temperature. It is also possible to prepare THP from HCN and DAP according to Chemische Berichte 98, pp. 1342–1349 (1965). Pyrimidine is then probably also formed from the THP intermediate, also when pure AFP is started from. AFP can be prepared, for instance, also according to the process described in FR-A No. 976959 from acrylonitrile and formamide, followed by hydrogenation in the presence of nickel or cobalt catalysts. Applicant has not been able to obtain certainty as to the reaction mechanism, and therefore the invention is not limited to any theory on this point.

Applicant has no explanation for the way in which DFP is converted to pyrimidine, but perhaps here, too, THP plays a part as intermediate, see for instance DE-A No. 3245109. The embodiment using a twofold molar excess of formamide relative to DAP via DFP is technologically attractive in that it does not require purification. The same holds for the preparation of 2-alkylpyrimidines with methyl or ethyl as alkyl group.

It is noted that the preparation of substituted pyrimidines starting from DAP and an alkane carboxylic acid amide, carried out in the gas phase in the presence of a palladium catalyst, is known from U.S. Pat. No. 4,376,201. In this known process, no carbon monoxide-hydrogen reactant is used, and the yield appears to vary between 5 and 9%, calculated on the molar amount of the amide.

The process according to the invention is preferably carried out at a temperature between 250° and 400° C., for then the pyrimidine yield is highest.

In one embodiment of the invention, the process for the preparation of pyrimidine is characterized in that it starts from the reaction product obtained by conversion of formamide with 1,3-diaminopropane in the liquid phase in a molar ratio of 0.1–10, optionally after separation of an excess of one or both starting materials.

The process according to the invention is carried out in the presence of a mixture of carbon monoxide and hydrogen, and/or a compound capable of at least partial decomposition into carbon monoxide and hydrogen under the reaction conditions. Examples of such compounds are alcohols such as methanol and ethanol. Such a substance or mixture will hereinafter be referred to as carbon monoxide-hydrogen reactant. The molar amount, calculated as the total of CO and $H_2$, generally is 0.5–100, preferably 2–50 times the amount of (alkyl)amidopropanes and/or (2-alkyl)-1,4,5,6-tetrahydropyrimidine to be converted. At an amount of carbon monoxide-hydrogen reactant smaller than a twofold molar excess, the (2-alkyl)pyrimidine yield decreases. Amounts in excess of a 50-fold molar excess offer no additional advantage, but require a relatively large reactor volume, which adversely affects the fixed costs of the process. The $CO:H_2$ ratio is not very critical and may vary from, for instance, 1:10 to 10:1.

Besides the carbon monoxide-hydrogen reactant, also an inert gas, for instance nitrogen or helium, can be passed through the reactor to achieve uniform evaporation of the starting mixture. Application of methanol and/or ethanol on the one hand has the advantage that it sensures uniform evaporation of the starting mixture, while on the other hand it is advantageous that under the reaction conditions a portion thereof decomposes into carbon monoxide and hydrogen in a proportion that is favourable to the reaction. Furthermore, it is advantageous that the starting compounds are well soluble in this type of alcohols, so that the starting compounds can in a simple way be converted to the gas phase.

In the process according to the invention palladium-containing catalysts are used. These catalysts generally contain 0.1–10 wt.% palladium, preferably 0.5–5 wt.%, calculated on the total catalyst. In addition, an alkali metal can be added to the catalyst, in amounts between 0.1 and 2 wt.%, calculated on the total catalyst.

The catalyst can be used on a carrier known per se. Such carriers may contain, for instance, aluminium oxide, carbon and silicon oxide. Aluminum oxide is preferred as a carrier because very good results are achieved.

Preferably, the catalyst is alkalimetal promoted, because in that case the life-time of the catalyst performance is increased.

Catalysts as described above usually are commercially available.

For practical realization of the process according to the invention, the embodiments of gas-phase reactions known per se can be used, for instance the embodiment in which the gaseous starting mixture is passed over the catalyst in the form of a solid bed or a so-called fluid bed. The space velocity may be varied, for instance between 0.001 and 2 g starting compound per milliliter catalyst material (bulk volume) per hour. The pressure at which the reaction in the gas phase takes place in itself is not important, so that the reaction will generally be carried out at autogenous pressure.

Working up of the (2-alkyl)pyrimidine obtained in the reaction can take place in a manner known per se by cooling followed by, for instance, distillation or extraction. These pyrimidines are used, inter alia, as intermediates in the synthesis of organic compounds such as crop protection agents.

The invention will be elucidated in the following examples.

EXAMPLE I

In a 5-liter round-bottom flask, 296.5 g (4.0 moles) 1,3-diaminopropane (DAP) was heated to 130° C. At this temperature subsequently 126 g (2.8 moles) formamide was added while stirring. The ammonia gas formed in the reaction was collected in dilute sulphuric acid, and titration showed the amount of ammonia formed to correspond with the amount of formamide metered, calculated on molar basis. After all formamide had been added, the excess DAP, together with some water formed during the reaction, was distilled off at 10 mbar. The DAP-water mixture collected was found to contain 1.84 moles DAP. The residue of 202 g was a mixture of AFP, THP and some DFP. per gramme of this starting mixture, 10.7 mmoles DAP were found to be incorporated (4.0–1.84 moles DAP in 202 g residue).

This starting mixture to be evaporated was dissolved in a 10-fold excess of methanol (0.107 mole ethanol per g starting mixture) and the resulting solution was brought at a temperature of 350° C. in an evaporator. The methanol-containing starting mixture was passed through a vertical tubular reactor (length 400 mm, diameter 20 mm), in which there was a zone of 20 ml catalyst. This was a Pd (1%)-Na (1%)-$Al_2O_3$ catalyst. The space velocity (LHSV) relative to the starting mixture was 0.23 ml per ml catalyst per hour. In addition, 3.6 l hydrogen per hour was passed through the reactor, on the one hand to achieve more uniform evaporation, and on the other to maintain a reducing environment in the catalyst bed.

The reaction gas was condensed and collected via a three-stage cooling system (12° C., 0° C. and −80° C.). The amount of pyrimidine was determined using gas-liquid chromatography (GLC) and the amount of condensed reaction product collected in a four-hour period. The pyrimidine yield was calculated on the basis of the amount of pyrimidine in the reaction product relative to the amount of DAP incorporated in the starting mixture. In doing so, the assumption that theoretically one mole pyrimidine can be formed per mole DAP was started from.

Table 1 gives the pyrimidine yields at various reaction times. The temperature of the catalyst bed in all cases was 350° C.

TABLE 1

| Operating time before sampling, in hours | Pyrimidine yield, in % |
| --- | --- |
| 4 | 54.3 |
| 24 | 51.7 |
| 47 | 54.0 |
| 115 | 52.0 |
| 143 | 50.2 |
| 188 | 51.6 |
| 215 | 49.0 |

EXAMPLE II

In the way described in Example I pyrimidine was prepared from the liquid starting mixture, the amount of methanol being varied. The amount of methanol is expressed in moles per mole of incorporated DAP (in the liquid starting mixture). Each experiment lasted 24 hours, after which the pyrimidine yield was determined from the amount of reaction product collected in this time. The results are presented in Table 2.

TABLE 2

| Amount of methanol, moles/mole incorporated DAP | Pyrimidine yield, in % |
|---|---|
| 0 | 23.2 |
| 2,5 | 41.3 |
| 5 | 48.6 |
| 10 | 53.6 |
| 20 | 54.8 |
| 30 | 52.2 |

EXAMPLE III

In the way described in Example II, ethanol was metered and varied instead of methanol. The results are presented in Table 3.

TABLE 3

| Amount of ethanol, moles/mole incorporated DAP | Pyrimidine yield, in % |
|---|---|
| 0 | 23.1 |
| 2,5 | 24.9 |
| 5 | 38.8 |
| 10 | 43.0 |
| 20 | 42.1 |
| 30 | 42.2 |

EXAMPLE IV

In the way described in Example II, a $CO/H_2$ mixture was metered instead of methanol. The results are presented in Table 4. It should be noted that the amount of metered hydrogen of 3.6 l per hour according to Example I is included in the amounts given in Table 4. In one case, therefore, no hydrogen at all was metered.

TABLE 4

| moles/mole incorporated DAP | | Pyrimidine yield, in % |
|---|---|---|
| $H_2$ | CO | |
| 0 | 6 | 14.3 |
| 6 | 3 | 47.0 |
| 7 | 0 | 31.4 |
| 11 | 3 | 56.3 |
| 12 | 6 | 51.0 |

EXAMPLE V

In the way described in Example I, 24-hour experiments were conducted at various temperatures and LHSV values. The results are presented in Table 5.

TABLE 5

| Temperature, °C. | LHSV ml/ml · hour$^{-1}$ | Pyrimidine yield, in % |
|---|---|---|
| 327 | 0.23 | 34.8 |
| 341 | 0.23 | 45.8 |
| 351 | 0.23 | 53.6 |
| 351 | 0.10 | 53.0 |
| 351 | 0.50 | 30.0 |
| 361 | 0.23 | 55.3 |

EXAMPLE VI

In the way described in Example I, pure THP instead of the starting mixture obtained in the liquid phase was dissolved in a 7-fold molar excess of methanol and the solution obtained was passed over the catalyst. The LHSV was 0.25 mol per mol catalyst per hour. In Table 6, the yields of pyrimidine, obtained by dehydrogenation of THP, at various reaction times are shown.

TABLE 6

| Operating time before sampling, in hours | Pyrimidine yield, in % |
|---|---|
| 4 | 56.1 |
| 24 | 55.7 |
| 48 | 54.6 |
| 72 | 55.0 |

EXAMPLE VII

In the way described in Example VI, instead of methanol an excess of a $CO/H_2$ mixture was metered, in a molar ratio relative to THP of 3 for CO and 7 for $H_2$. As in Example IV, the excess of $H_2$ includes all hydrogen metered. After 24 hours reaction time, a pyrimidine yield of 58.8% was recorded.

EXAMPLE VIII

Example VII was repeated with a molar excess of CO and $H_2$ relative to THP of 3.3 and 10, respectively. After 24 hours the pyrimidine yield was 57.3%.

EXAMPLE IX

In the way described in Example I, a liquid-phase reaction of 360 g formamide (8.0 moles) and 296.5 g DAP (4.0 moles) was carried out. This yielded 503 g DFP. This DFP was dissolved in a 10-fold molar excess of methanol and passed to the evaporator. The gas-phase reaction was further carried out as described in Example I at an LHSV of 0.20 ml per mol catalyst per hour. The pyrimidine yields after various reaction times are given in Table 7.

TABLE 7

| Operating time before sampling, in hours | Pyrimidine yield, in % |
|---|---|
| 6 | 45.1 |
| 20 | 44.3 |
| 50 | 43.4 |

EXAMPLE X

Using the starting mixture and the reaction conditions as described in Example I, 24-hour gas-phase reactions were carried out with various catalysts to determine the pyrimidine yields. The results are presented in Table 8.

TABLE 8

| Catalyst Pd in wt. % | Pyrimidine yield, in % |
|---|---|
| Pd (1%) - $Al_2O_3$ | 59.0 |
| Pd (0,5%) - $Al_2O_3$ | 56.3 |
| Pd (2,0%) - $Al_2O_3$ | 52.2 |
| Pd (0,5%) - $ZrO_2$ | 43.5 |
| Pd (0,5%) - $ZnO_2$ | 25.3 |
| Pd (0,5%) - $ZnO_2/Al_2O_3$ | 50.1 |
| Pd (0,5%) - MgO | 24.0 |
| Pd (1%) - $SiO_2$ | 4.3 |

TABLE 8-continued

| Catalyst Pd in wt. % | Pyrimidine yield, in % |
|---|---|
| Pd (1%) - LiAl$_5$O$_8$ spinel | 15.6 |

EXAMPLE XI

Purified AFP was prepared by coupling of formamide and acrylonitrile as described in FR-A No. 976959 followed by hydrogenation in the liquid phase at elevated pressure in an alkaline ammoniacal environment using a cobalt catalyst. The purified AFP was dissolved in a 10-fold excess of methanol in accordance with Example I before being passed, via the evaporator, in the gas phase over the catalyst. The condensation product was collected during 16 hours and analyzed for pyrimidine. The yield was found to be 49.7%, calculated on AFP.

EXAMPLE XII

In a long-duration experiment of 205 hours, performed according to Example I, 1 kg starting mixture was dissolved in 3.4 kg methanol and passed in the gas phase over the catalyst via the evaporator. In total, 3.52 kg condensated product was collected, which was found to contain 442 g pyrimidine. Purification of this pyrimidine by distillation yielded 397 g pyrimidine with a melting point of 21°–22° C. and a purity of more than 99.7%. The water content was less than 0.01 wt.%.

EXAMPLE XIII

A. At 70° C., 123 g acetic acid anhydride was gradually, dropwise, added to 111 g diaminopropane, dissolved in 200 ml ethanol.

The reaction mixture obtained was subsequently distilled. After removal of the ethanol, a fraction of 23.9 g destillate was still obtained, which consisted almost exclusively of water. At 164°–180° C. and 0.9 mm Hg 136.8 g of a mixture was obtained which consisted of approx. 10 wt.% 2-methyl-1,4,5,6-tetrahydropyrimidine and approx. 90 wt.% of the corresponding acetic acid salt of 2-methyl-1,4,5,6-tetrahydropyrimidine, corresponding with approx. 0.87 mole in total of the tetrahydropyrimidine.

The distillation residue almost exclusively contained the diamide of diaminopropane, viz. 1,3-diacetamidopropane.

B. Of the pyrimidine mixture described in A., 130 g was dissolved in 270 g methanol. The solution obtained was passed, at a flow rate of 21 g/h, via an evaporator over a catalyst bed of 20 g. Both the evaporator and the catalyst bed were kept at a temperature of 350° C. The same catalyst as described in Example I was placed in a tubular reactor having an internal diameter of 20 mm.

To maintain a reducing environment, also 2.5 l/h hydrogen gas was passed over the catalyst via the evaporator. The reaction gases were condensed in a two-stage cooling system (12° C., 0° C.) and collected. GLC analysis showed the fully condensed reaction product to contain 67.2 g of the desired 2-methyl-pyrimidine. Distillation yielded 60.2 g of the pure 2-methyl-pyrimidine.

EXAMPLE XIV

In a manner analogous with that described in Example XIII A, a larger amount (600 g) of the desired mixture of 2-methyl-1,4,5,6-tetrahydropyrimidine and the corresponding acetic acid salt was obtained.

At a flow rate of 20 g/h, a 25% solution of this mixture in ethanol was passed over the catalyst via an evaporator. In addition, 2 l/h hydrogen gas was passed over.

The catalyst consisted of a bed of 20 g Pd (1%)-Na (1%)-Al$_2$O$_3$, which was maintained at a temperature of 330° C., as was the evaporator. The reaction gases were condensed in a two-stage cooling system.

As a function of time, samples were taken during a four-hour period.

The samples were weighed and subjected to GLC analysis, and the yield was calculated as mole percents 2-methylpyrimidine, analyzed in a four-hour period in the reaction product, relative to the mole percents 2-methyl-1,4,5,6-tetrahydropyrimidine metered in the same period of time.

Table 9 presents the results. As time, the number of hours before sampling is given.

TABLE 9

| Time (hours) | 2-methylpyrimidine yield in % |
|---|---|
| 6 | 85 |
| 20 | 88 |
| 50 | 89 |
| 70 | 89 |
| 100 | 88 |

The off-gas was also analyzed regularly; besides H$_2$ (approx. 30%), it contained CO and CH$_4$ in equal amounts of also approx. 30%, while also some CO$_2$ (1%) could be analyzed. The CO and CH$_4$ content decreased somewhat with time.

EXAMPLE XV

At a flow rate of 20 g/h, a 20% solution of 2-ethyl-1,4,5,6-tetrahydropyrimidine in methanol was passed over the catalyst, analogously with Example XIV. (The 2-ethyl-1,4,5,6-tetra-hydropyrimidine can be prepared, inter alia, from diaminopropane and propionic acid). After condensation of the reaction product, this compound, too, was found to be capable of being hydrogenated to the corresponding 2-ethyl-pyrimidine in a yield of 85% during a 40-hour experiment.

We claim:
1. A process for the preparation of pyrimidine compounds of formula 1

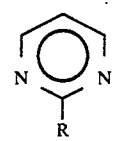

wherein R=H, CH$_3$ or C$_2$H$_5$, comprising the steps of
(A) carrying out a gas phase reaction over a palladium-containing catalyst in the presence of a carbon monoxide-hydrogen reactant at a temperature of between 200° and 550° C., the reactant mixture comprising
 (1) in case R=H, at least one compound chosen from the group consisting of
  (a) the liquid phase reaction product of formamide with 1,3-diaminopropane,
  (b) 1-amino-3-formamidopropane,
  (c) 1,4,5,6-tetrahydropyrimidine, and
  (d) 1,3-diformamidopropane;

(2) in case R=CH₃, at least one compound chosen from the group consisting of
  (a) 1-amino-3-acetamidopropane,
  (b) 2-methyl-1,4,5,6-tetrahydropyrimidine, and
  (c) 1,3-diacetamidopropane;
(3) in case R=C₂H₅, at least one compound chosen from the group consisting of
  (a) 1-amino-3-propionamidopropane,
  (b) 2-ethyl-1,4,5,6-tetrahydropyrimidine, and
  (c) 1-3-diproprionamidopropane; and
(B) recovering a pyrimidine compound of formula 1.

2. The process for preparation of pyrimidine compounds according to claim 1, wherein the reactant mixture in step (A) comprises a liquid phase reaction product of formamide with 1,3-diaminopropane from which the excess formamide or 1,3-diaminopropane has been removed.

3. The process according to claim 1, wherein the gas-phase reaction is carried out at a temperature between 250° and 400° C.

4. The process according to claim 1, wherein the carbon monoxide-hydrogen reactant is present in a 2-50-fold molar excess, calculated relative to the one or more (alkyl)amidoaminopropane, di(alkyl)amidopropane or (alkyl)tetrahydropyrimidine compounds which comprise the reactant mixture.

5. The process according to claim 1, wherein methanol or ethanol is the carbon monoxide-hydrogen reactant.

6. The process according to claim 1, wherein the catalyst contains 0.5–5 wt.% palladium, calculated on the total catalyst.

7. The process according to claim 1, wherein the catalyst contains 0.1–2 wt.% alkali metal, calculated on the total catalyst.

8. The process according to claim 1, wherein the catalyst contains a carrier of aluminum oxide.

9. The process for the preparation of pyrimidine compound according to claim 1, wherein the reactant mixture in step (A) comprises the liquid phase reaction product of formamide with 1,3-diaminopropane in a molar ratio of 0.1–10, from which the excess formamide or 1,3-diaminopropane has been removed.

* * * * *